(12) United States Patent
Lee

(10) Patent No.: US 7,037,326 B2
(45) Date of Patent: May 2, 2006

(54) SKIN COOLING DEVICE USING THERMOELECTRIC ELEMENT

(76) Inventor: Hee-Young Lee, Kangnam Plastic Surgery, 12-7, Jungang-ro 1st, Kunsan-si, Jeonrabuk-do, 573-041 (KR)

( * ) Notice: Subject to any disclaimer, the term of this patent is extended or adjusted under 35 U.S.C. 154(b) by 6 days.

(21) Appl. No.: 10/388,775

(22) Filed: Mar. 14, 2003

(65) Prior Publication Data

US 2004/0181269 A1 Sep. 16, 2004

(51) Int. Cl.
*A61F 7/00* (2006.01)

(52) U.S. Cl. .......................... 607/108; 606/20; 607/109

(58) Field of Classification Search ............ 606/20–23; 607/96, 98, 104, 109
See application file for complete search history.

(56) References Cited

U.S. PATENT DOCUMENTS

| | | | | |
|---|---|---|---|---|
| 3,133,539 A | * | 5/1964 | Eidus ........................... | 607/96 |
| 3,207,159 A | * | 9/1965 | Tateisi ......................... | 607/96 |
| 4,930,317 A | * | 6/1990 | Klein ........................... | 62/3.3 |
| 5,097,828 A | * | 3/1992 | Deutsch ....................... | 607/104 |
| 6,017,337 A | * | 1/2000 | Pira ............................. | 606/20 |
| 6,023,932 A | * | 2/2000 | Johnston ...................... | 62/3.5 |
| 6,196,839 B1 | * | 3/2001 | Ross ............................ | 433/3 |
| 6,567,696 B1 | * | 5/2003 | Voznesensky et al. ......... | 607/3 |

* cited by examiner

*Primary Examiner*—Roy D. Gibson
(74) *Attorney, Agent, or Firm*—Dilworth & Barrrese, LLP

(57) ABSTRACT

Disclosed is a skin cooling device which utilizes the sensory ability of the skin as an integumentary sense organ so that it is applicable to medical treatments and surgical operations, while being configured to use the heat absorbing effect of a thermoelectric element while having a small size to be easily handled. The skin cooling device includes a case having a size allowing the user to grasp the case by the hand, and a thermoelectric element installed in the case. The thermoelectric element has a heat emitting portion and a heat absorbing portion. The skin cooling device also includes a heat sink unit provided at the heat emitting portion of the thermoelectric element, and cold heat transfer unit provided at the heat absorbing portion of the thermoelectric element, and adapted to locally transfer cold heat from the thermoelectric element to the skin. Thus, the cold heat can be locally applied to the skin.

12 Claims, 9 Drawing Sheets

SKIN COOLING DEVICE USING THERMOELECTRIC ELEMENT

BACKGROUND OF THE INVENTION

1. Field of the Invention

The present invention relates to a skin cooling device which utilizes the sensory ability of the skin as an integumentary sense organ so that it is applicable to medical treatments and surgical operations, and more particularly to a skin cooling device which is configured to use the heat absorbing effect of a thermoelectric element while having a small size to be easily handled.

2. Description of the Related Art

Cooling the human body makes it possible to obtain various effects such as alleviation of pain, constriction of blood vessels, and suppression of inflammatory reaction. Although appliances for generating such a cooling effect have been proposed, they are used only in limited fields, due to diverse reasons.

For example, cooling devices have been proposed which are applied to a skin cooling method for medical treatment of skin troubles or medical treatment using a laser. In the case of a cooling device applied to medical treatment of skin troubles, it is configured to use heat of vaporization generated during vaporization of liquid nitrogen. However, this cooling device has a disadvantage in that it cannot be easily handled under general surgical operation conditions because of its complex configuration. In the cooling device, it is also difficult to achieve an easy temperature control. Furthermore, there is inconvenience in use because the use time is limited due to the vaporization rate of the liquid nitrogen. On the other hand, in the case of a cooling device applied to medical treatment using a laser, it is configured to apply cold air, supplied from a cooling unit via a tube, to a body portion to be surgically operated. However, this cooling device is bulky and expensive. Furthermore, there is inconvenience in that the cooling device has a low cooling speed.

For this reason, the above mentioned cooling devices have been used in very limited fields, for example, only in surgical operation fields. In particular, these cooling devices cannot achieve easy cooling of a very small area of skin. Since the conventional cooling devices are configured to utilize a compressed refrigerant or heat of vaporization, their configurations are complex. As a result, these cooling devices are very inconvenient to use for medical treatment and surgical operation purposes.

SUMMARY OF THE INVENTION

Therefore, an object of the invention is to provide a cooling device which is capable of locally cooling the human body so that it is easily applicable to surgical operations and medical treatment of skin troubles and other troubles.

Another object of the invention is to provide a skin cooling device having a simple configuration so as to be easily handled while being capable of rapidly obtaining a desired cooling effect, and having a size-reduced and inexpensive construction so as to be effectively used for treatment of pimples and pain alleviation or treatment of skin rash and insect bites, not only in general surgical operation fields, but also in the home.

Another object of the invention is to provide a skin cooling device which can reduce, as much as possible, the operation delay time caused by selection and handling of surgical instruments required for a series of operations to be carried out in an operating room for alleviation of pain at the body portion being operated and removal of foreign matters during a surgical operation such as a surgical operation using a laser, thereby achieving an enhancement in the efficiency of surgical operations, and a reduction in operating time.

In accordance with the present invention, these objects are accomplished by providing a skin cooling device comprising: a case having a size allowing a user to grasp the case by the hand; at least one thermoelectric element installed in the case, the thermoelectric element having a heat emitting portion and a heat absorbing portion; heat sink means provided at the heat emitting portion of the thermoelectric element; and cold heat transfer means provided at the heat absorbing portion of the thermoelectric element, and adapted to locally transfer cold heat from the thermoelectric element to the skin, whereby the cold heat is locally applied to the skin.

In this configuration, the thermoelectric element is adapted to utilize a thermoelectric phenomenon in which an exothermic reaction is generated at one side of the thermoelectric element, and an endothermic reaction (cooling) is generated at the other side of the thermoelectric elements in accordance with the polarities of DC current applied to the thermoelectric material of the thermoelectric element. This element is used to obtain both the cooling and heating effects, or to achieve an exchange of heat with electricity in heat power generation fields.

The present invention is applied to cooling of the skin by utilizing the heat absorbing phenomenon occurring at the thermoelectric element. Heat sink means is provided at the heat emitting portion of the thermoelectric element, whereas cold heat transfer means is provided at the heat absorbing portion of the thermoelectric element to transfer cold heat to the skin. The heat absorbing temperature varies depending on the heat sink efficiency of the thermoelectric element. The thermoelectric element and heat sink means are configured to adjust the cooling temperature within a range of 3° C. to −30° C.

The heat sink means may be of either an air cooling type or a water cooling type. The cold heat transfer means may be of a skin contact type using a contact tip made of a heat transferring metallic material or a cold air application type using a fan.

The case has a rectangular shape having a size allowing the user to grasp the case by the hand while carrying the heat sink means, cold heat transfer means, and thermoelectric element. There is no particular limitation on the outer structure of the case.

BRIEF DESCRIPTION OF THE DRAWINGS

The above objects, and other features and advantages of the present invention will become more apparent after a reading of the following detailed description when taken in conjunction with the drawings, in which.

DESCRIPTION OF THE PREFERRED EMBODIMENTS

Figure 1:
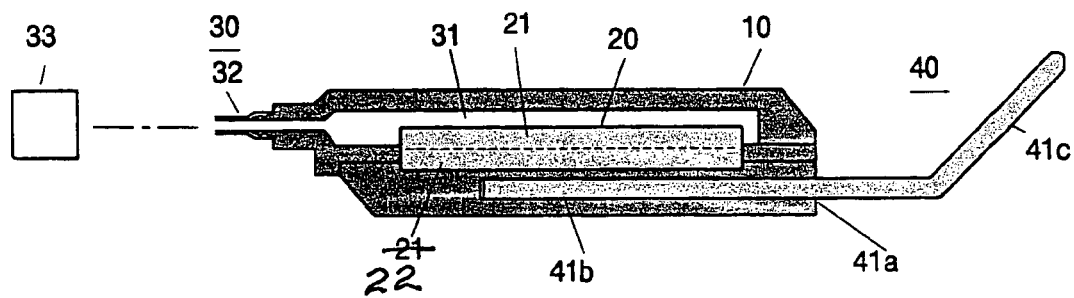
FIG. 1 is a sectional view of a skin cooling device according to an embodiment of the present invention, illustrating an internal configuration of the skin cooling device.
Figure 2:
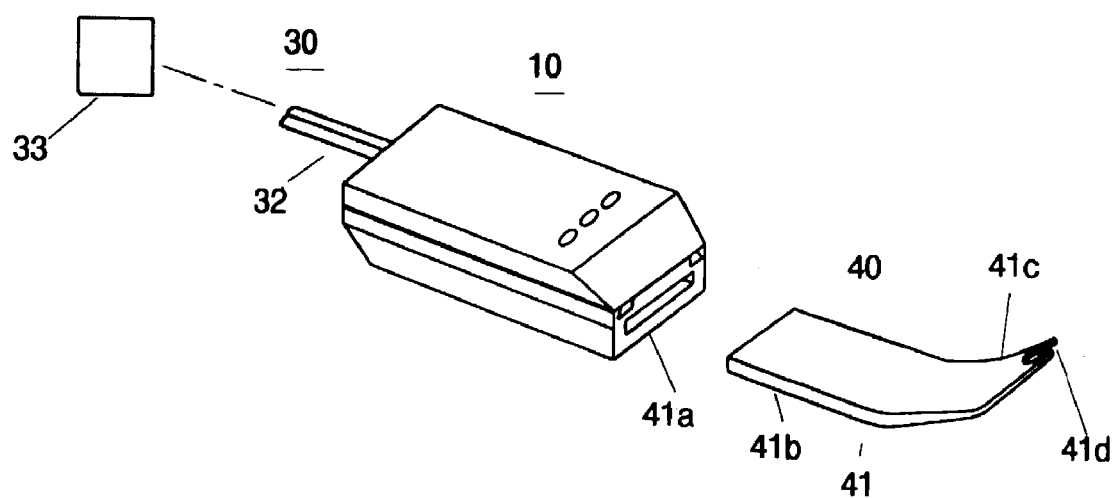
FIG. 2 is an exploded perspective view of the skin cooling device, illustrating an external configuration of the skin cooling device.

FIGS. 1 and 2 illustrate a skin cooling device according to an embodiment of the present invention. In accordance with the embodiment of the present invention, the skin cooling device basically includes a case 10 having a rectangular shape, at least one thermoelectric element 20 installed in the case 10, a heat sink unit 30 arranged at an upper heat emitting portion 21 of the thermoelectric element 20, and a cold heat transfer unit 40 coupled to a lower heat absorbing portion 22 of the thermoelectric element 20.

The case 10 has a size of 8 cm×5 cm×2 cm in width, length, and thickness. The case 10 of such a size may receive three or four thermoelectric elements each having a size of 0.8 cm×0.8 cm ×0.5 cm, or one or two thermoelectric elements of a larger size.

A space 31 is defined in the case 10 over the thermoelectric element 20. A DC voltage source is connected across the thermoelectric element 20 such that the upper and lower portions of the thermoelectric element 20 serve as a heat emitter and a heat absorber, respectively.

The space 31 defined over the thermoelectric element 20 is provided for the heat sink unit 30. In the illustrated embodiment, the heat sink unit is of a water cooling type.

That is, two tubes 32 are each connected at one end thereof to the case 10 such that it communicates with the space 31. Each tube 32 is also connected at the other end thereof to an external cooling unit 33.

The heat sink unit 30 radiates heat, and transfers the radiated heat to water from the cooling unit 33 circulating through the space 31. Accordingly, a superior heat sink effect is obtained over an air cooling type structure. When current flows through the thermoelectric element 20, a heat absorbing effect is generated at the thermoelectric element 20 in proportion to the heat sink ability of the thermoelectric element 20. Accordingly, it is possible to widen the effective cooling temperature range of the cooling device.

The heat sink unit 30 influences the heat absorption efficiency of the thermoelectric element 20. Accordingly, where the heat sink unit 30 is of a water cooling type, it is possible to lower the cooling temperature of the heat sink unit 30 by lowering the temperature of the water circulating through the heat sink unit 30.

In this regard, it is preferable to provide a heat exchanger at the cooling unit so as to sufficiently lower the temperature of the cooling water. The cooling unit may be configured using a thermoelectric element having a heat absorbing portion coming into contact with circulating cooling water so that it has a reduced size.

Figure 3:
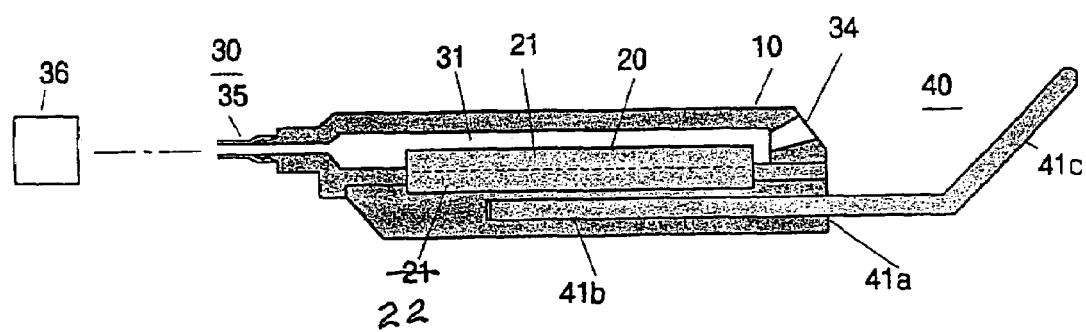
FIG. 3 is a sectional view illustrating another embodiment of the present invention in which an air cooling type heat sink unit is used.

In accordance with the present invention, the heat sink unit may be of an air cooling type, in place of the water cooling type. In this case, an air inlet 34 may be formed at the case 10 to communicate with the space 31, so as to introduce external air into the space 31, as shown in FIG. 3. A tube 35 is connected at one end thereof to the case 10 to communicate with the space 31. The tube 35 is also connected to an external exhaust unit 36 at the other end thereof.

The cold heat transfer unit 40 is coupled to the lower portion 22 of the thermoelectric element 20 serving as a heat absorber.

The cold heat transfer unit 40 may have diverse types. Taking into consideration practical applications and sterility, the cold heat transfer unit may be of a skin contact type, a cold air application type, in which cold air is applied to the skin, or a combined type thereof In the embodiment illustrated in FIGS. 1 and 2, the cold heat transfer unit 40 is of the skin contact type in which a skin contact tip 41 is used. In accordance with this embodiment, a tip fitting hole 41a is formed at a portion of the case 10 contacting the bottom of the heat absorber 22. The skin contact tip 41 is separably fitted in the tip fitting hole 41a at one end thereof. Thus, cold heat can be transferred to the skin contact tip 41.

The skin contact tip 41 has a fitting portion 41b, and a skin contact portion 41c, and is made of a metal having a high thermal conductivity, for example, silver, copper, or aluminum.

The skin contact tip 41 comes into indirect contact with the heat absorbing portion 22 of the thermoelectric element 20 at the fitting portion 41b thereof, so that cold heat from the thermoelectric element 20 is transferred to the skin contact portion 41c which, in turn, directly applies the transferred cold heat to the skin.

Figure 4A:
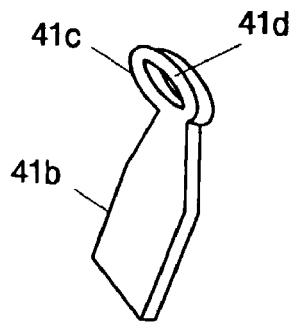
FIGS. 4a to 4c are perspective views respectively illustrating skin contact tips according to different embodiments of the present invention.
Figure 4B:
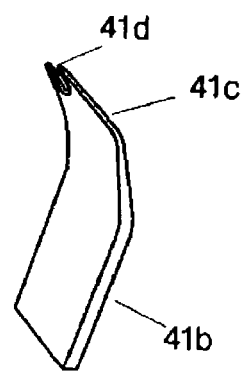
Figure 4C:
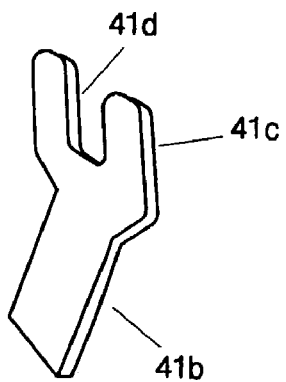

The skin contact portion 41c of the skin contact tip 41 may have diverse shapes, taking into consideration the keenness of the integumentary sense organ. FIGS. 4a to 4c illustrate various embodiments of the skin contact tip, respectively.

As shown in FIGS. 4a to 4c, the skin contact tip is configured to have a circular hole or "U"-shaped groove 41d. This hole or groove 41d serves to alleviate pain on the basis of the keenness of the integumentary sense organ.

The second finger having a keenest intergumentary sense organ can recognize stimuli at two points spaced about 2.5 mm or more apart. For this reason, when the second finger is pricked with two needles at points spaced less than 2.5 mm apart, respectively, it cannot recognize both of the pricked points, but recognizes only one point. In the case of the face skin, the distance of about 5 mm or more can be recognized. For this reason, when a stimulus is applied to the face skin within a region defined by the hole or groove of the skin contact tip under the condition in which the skin contact tip in a cold state is in contact with the face skin, it is difficult for the face skin to distinguish the stimulus from the cold applied thereto. Accordingly, the pain upon popping a pimple, removing a spot, or getting a shot cannot be recognized.

Thus, the above described skin contact tip can be applied in various manners to surgical operations and practical life.

Figure 5:
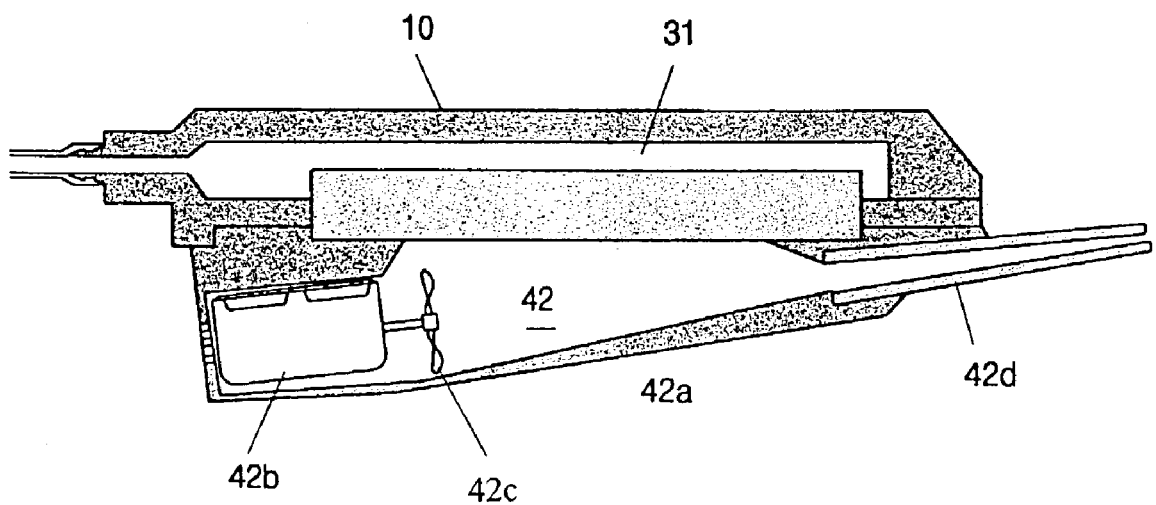
FIG. 5 is a sectional view illustrating another embodiment of the present invention in which a cold air application type cold heat transfer unit is used.

FIG. 5 illustrates another embodiment of the present invention in which a cold air application type cold heat transfer unit 42 is used. In accordance with this embodiment, the cold heat transfer unit 42 includes a space 42a defined beneath the lower heat absorbing portion 22 of the thermoelectric element 20, a motor 42b installed in the space 42a, a fan 42c installed in the space 42a, and coupled to the motor 42b, and a cold air guide tube 42d connected to an outlet formed at the space 42a while extending outwardly from the outlet.

In accordance with this configuration, cold heat generated from the thermoelectric element 20 is outwardly discharged via the cold air guide tube 42d in accordance with a blowing operation of the fan 42c so that it is applied to the skin. This cooling device can locally cool the skin to alleviate pain generated during a surgical operation while simultaneously removing fumes or odor generated during an electro-cauterization or a medical treatment using a laser. It is also possible to localize the reactive hyperemia phenomenon exhibited after the cooling of the skin, thereby actively limiting increase of blood flow, increased absorption of a skin coating agent, and secretion of an inflammatory substance such as histamine. Accordingly, there is an effect of suppressing an inflammatory reaction immediately following a skin trauma such as a wound or a sting by an insect. Thus, the cooling device of this embodiment can be advantageously applied to practical life.

Figure 6:
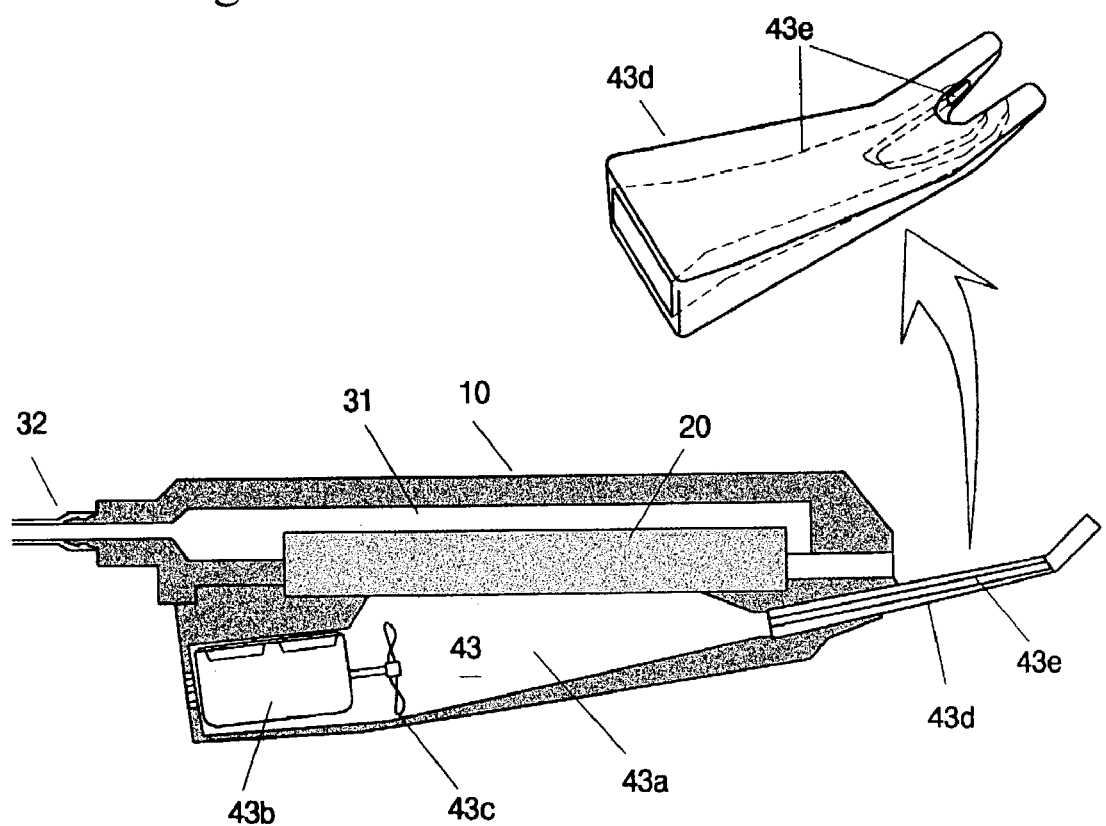
FIG. 6 is a sectional view illustrating another embodiment of the present invention in which a cold heat transfer unit having a combined type of a skin contact type and a cold air application type is used, while illustrating a part of the cold heat transfer unit in the form of a perspective view.
Figure 7A:
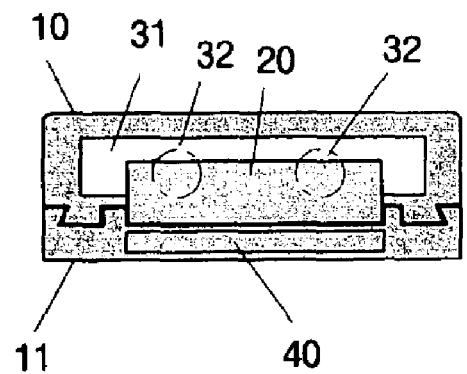
FIGS. 7a to 7d are sectional views respectively illustrating configurations in which respective cold heat transfer units are configured to be of a detachable type.
Figure 7B:
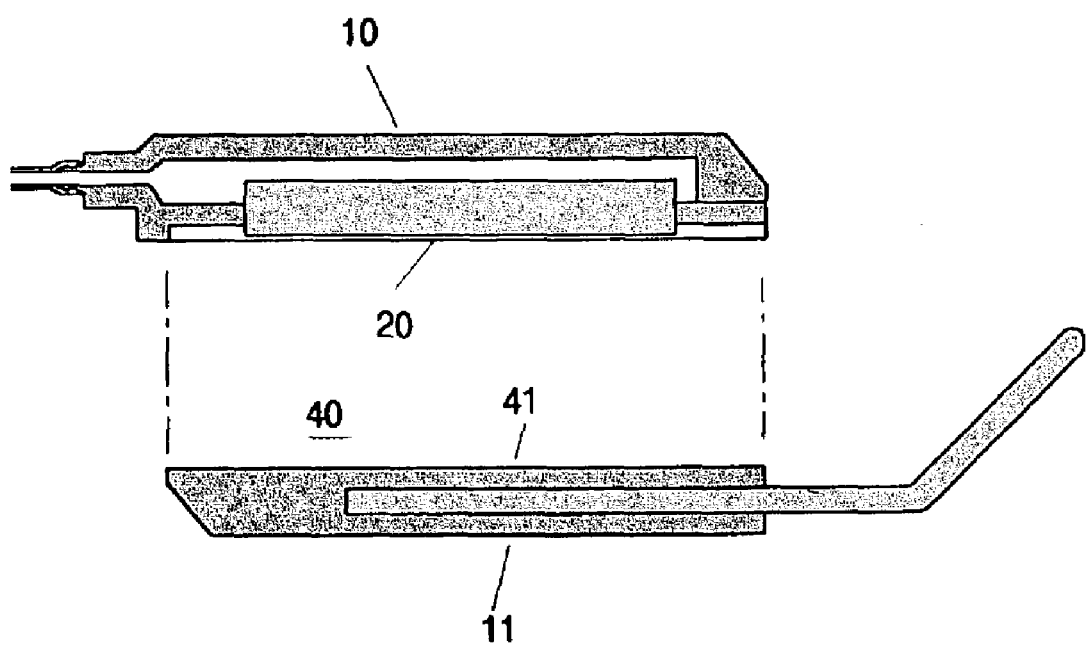
Figure 7C:
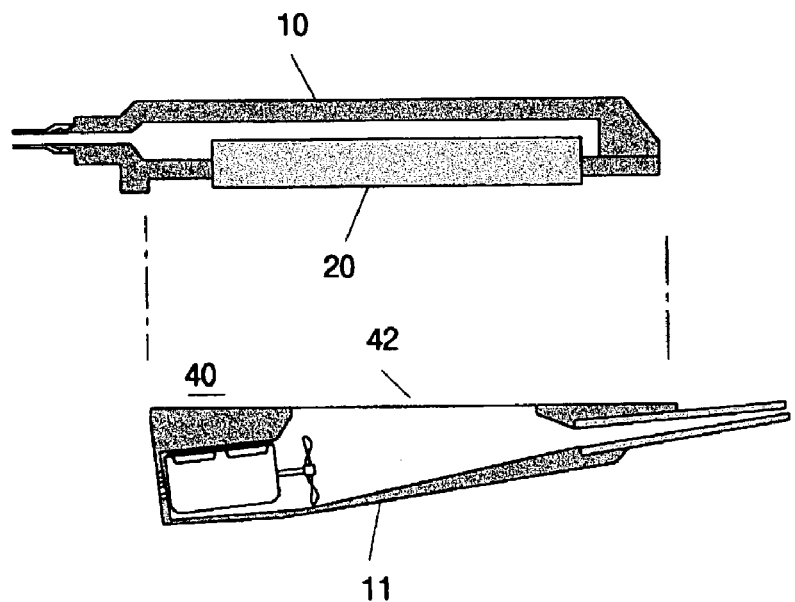
Figure 7D:
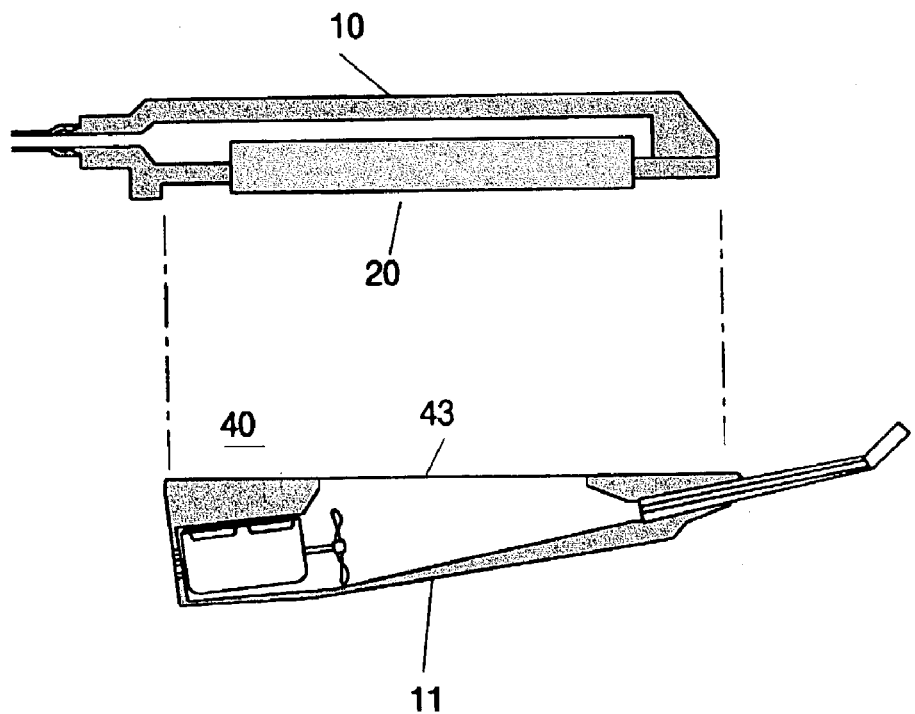

FIG. 6 illustrates another embodiment of the present invention in which a cold heat transfer unit 43 having a combined type of the skin contact type and the cold air application type is used. In accordance with this embodiment, the cold heat transfer unit 43 includes a space 43a defined beneath the lower heat absorbing portion 22 of the thermoelectric element 20, a motor 43b installed in the space 43a, a fan 43c installed in the space 43a, and coupled to the motor 43b, a skin contact tip 43d connected to an outlet formed at the space 43a, and a cold air guide passage 43e defined in the skin contact tip 43d so as to allow cold air from the space 43a to be outwardly discharged from an outlet end of the skin contact tip 43d.

In accordance with this configuration, the skin is cooled by bringing the skin contact tip 43d into contact with the skin while simultaneously applying cold air to the skin. Accordingly, the advantages of both the skin contact type and the cold air application type are obtained.

FIGS. 7a to 7d illustrate configurations for achieving effective use of the cold heat transfer unit while allowing the cold heat transfer unit to be replaceable with another type, that is, the skin contact type, cold air application type or combined type, if necessary, respectively. In either configuration, the lower heat absorbing portion of the thermoelectric element mounted in the case 10 is exposed in a downward direction. A lower case 11 is provided which is detachably coupled to the case 10 to cover the lower portion of the thermoelectric element. A cold heat transfer unit 41, 42, or 43 of the skin contact type, cold air application type or combined type is mounted in the case 10.

In accordance with these configurations, it is possible to use a common upper construction while using various types of cold heat transfer units. Accordingly, it is possible to replace the cold heat transfer unit with a desired type in accordance with the body portion to be operated or treated.

Figure 8A:
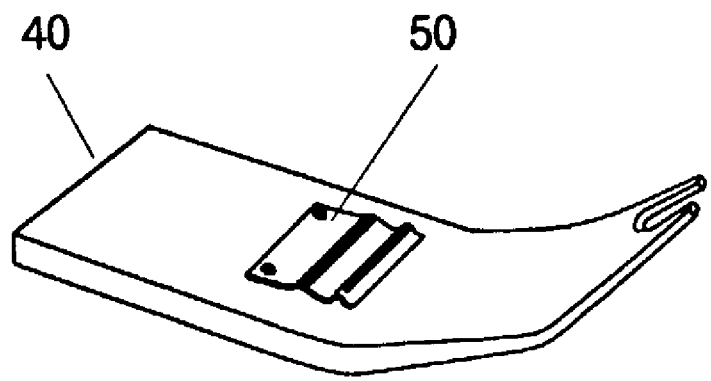
FIGS. 8a and 8b are views respectively illustrating clips provided at respective cold heat transfer units in accordance with embodiments of the present invention.
Figure 8B:
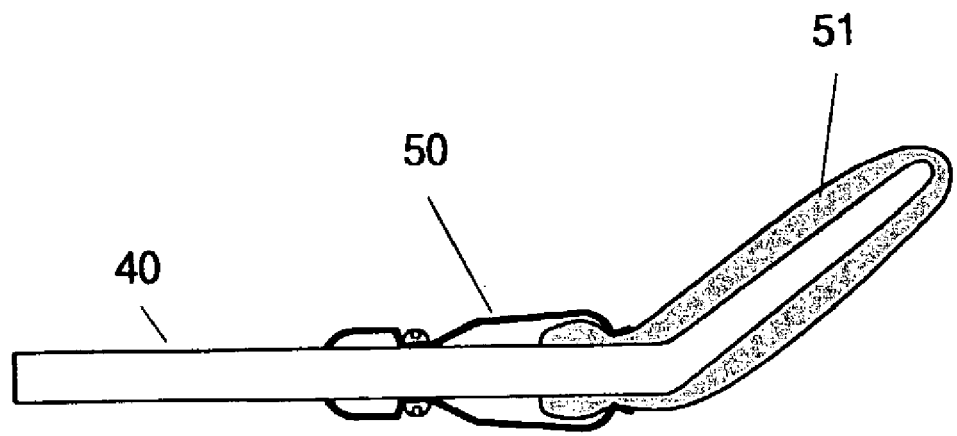

FIGS. 8a and 8b illustrate clips 50 for holding sterilized cottons or gauzes 51 at the skin contact tip 41 or 43d and the cold air guide tube 42 of the cold heat transfer unit, respectively.

In accordance with this configuration, the user can conveniently perform a surgical operation while simultaneously cooling the skin and cleaning the body portion being operated, using the cooling device of the present invention, under the condition in which he holds a laser surgical instrument or an electro-cauterizer in one hand while holding, in the other hand, the cooling device with a sterilized cotton or gauze being held between upper and lower portions of the clip 50, without using any separate instrument for clipping the sterilized cotton or gauze to clean the body portion being operated. Accordingly, the user can devote himself to the surgical operation. Also, it is possible to achieve an enhancement in the efficiency of the surgical operation, and a reduction in operation time.

The above described configuration according to the present invention is adapted to effectively conduct local cooling of the skin by utilizing a thermoelectric effect generated by the thermoelectric element. Although the preferred embodiments of the present invention have been disclosed for illustrative purposes, those skilled in the art will appreciate that various modifications, additions and substitutions are possible, without departing from the scope and spirit of the invention as disclosed in the accompanying claims. For example, various embodiments may be implemented in association with the shape of the case, the heat sink unit, and the cold heat transfer unit.

In accordance with the present invention, it is also possible to obtain an effect of locally stimulating the skin by hot heat by changing the polarity of current applied to the thermoelectric element while using the same configuration, by virtue of the characteristics of the thermoelectric element. It will be appreciated that such a change pertains to another application of the present invention, and falls within the scope of the invention.

As apparent from the above description, the present invention provides a cooling device which is capable of locally cooling the human body so that it is easily applicable to surgical operations and medical treatment of skin troubles and other troubles. The cooling device of the present invention has a simple configuration so as to be easily handled while being capable of rapidly obtaining a desired cooling effect. The cooling device also has a size-reduced and inexpensive construction so as to be effectively used for treatment of pimples and pain alleviation or treatment of skin rash and insect bites, not only in general surgical operation fields, but also in the home.

In accordance with the present invention, it is also possible to reduce, as much as possible, the operation delay time caused by selection and handling of surgical instruments required for a series of operations to be carried out in an operating room for alleviation of pain at the body portion being operated and removal of foreign matters during a surgical operation such as a surgical operation using a laser, thereby achieving an enhancement in the efficiency of surgical operations, and a reduction in operating time.

What is claimed is:

1. A skin cooling device comprising:
   a case having a size allowing a user to grasp the case by hand;
   at least one thermoelectric element installed in the case, the thermoelectric element having a heat emitting portion and a heat absorbing portion;
   heat sink means provided at the heat emitting portion of the thermoelectric element; and
   cold heat transfer means provided at the heat absorbing portion of the thermoelectric element, and adapted to locally transfer cold heat from the thermoelectric element to the skin, wherein the cold heat transfer means comprises:
   a confined space provided at the heat absorbing portion of the thermoelectric element;
   a motor installed in the space;
   a fan installed in the space, and coupled to the motor;
   a cold air guide tube connected to an outlet formed at the space while extending outwardly from the outlet, whereby the cold heat transfer means is of a cold air application type for applying the cold air to the skin.

2. The skin cooling device according to claim 1 further comprising a lower case detachably coupled to the case to cover the heat absorbing portion of the thermoelectric element, the lower case carrying the cold heat transfer means therein, whereby the skin cooling device can have a common upper construction while being capable of using various types of cold heat transfer means by replacing the lower case with another one carrying another type of cold heat transfer means, wherein the heat absorbing portion of the thermoelectric element is exposed from the case in a downward direction.

3. The skin cooling device according to claim 1 wherein the cold heat transfer means is provided with a clip for holding a sterilized cotton or gauze at the cold heat transfer means.

4. The skin cooling device according to claim 1, wherein the heat sink means comprises:
    a confined space provided at the heat emitting portion of the thermoelectric element; and
    two tubes each connected at one end thereof to the case such that it communicates with the space, each tube being connected at the other end thereof to an external cooling unit, whereby discharge of heat from the heat sink means is carried out in accordance with circulation of water in the space.

5. The skin cooling device according to claim 1, wherein the heat sink means comprises:
    a confined space provided at the heat emitting portion of the thermoelectric element;
    an air inlet formed at the case to communicate with the space; and
    a tube connected at one end thereof to the case to communicate with the space, the tube being connected to an external exhaust unit at the other end thereof, whereby discharge of heat from the heat sink means is carried out in accordance with exhaustion of air from the space.

6. A skin cooling device comprising:
    a case having a size allowing a user to grasp the case by hand;
    at least one thermoelectric element installed in the case, the thermoelectric element having a heat emitting portion and a heat absorbing portion;
    heat sink means provided at the heat emitting portion of the thermoelectric element; and
    cold heat transfer means provided at the heat absorbing portion of the thermoelectric element, and adapted to locally transfer cold heat from the thermoelectric element to the skin, wherein the cold heat transfer means comprises:
    a confined space provided at the heat absorbing portion of the thermoelectric element;
    a motor installed in the space;
    a fan installed in the space, and coupled to the motor;
    a skin contact tip connected to an outlet formed at the space; and
    a cold air guide passage defined in the skin contact tip to allow cold air from the space to be outwardly discharged from an outlet end of the skin contact tip, whereby the cold heat transfer means is of a combined type for cooling the skin by bringing the skin contact tip into contact with the skin while simultaneously applying cold air to the skin.

7. The skin cooling device according to claim 6 further comprising a lower case detachably coupled to the case to cover the heat absorbing portion of the thermoelectric element, the lower case carrying the cold heat transfer means therein, whereby the skin cooling device can have a common upper construction while being capable of using various types of cold heat transfer means by replacing the lower case with another one carrying another type of cold heat transfer means wherein the heat absorbing portion of the thermoelectric element is exposed from the case in a downward direction.

8. The skin cooling device according to claim 6 wherein the cold heat transfer means is provided with a clip for holding a sterilized cotton or gauze at the cold heat transfer means.

9. The skin cooling device according to claim 6, wherein the heat sink means comprises:
    a confined space provided at the heat emitting portion of the thermoelectric element; and
    two tubes each connected at one end thereof to the case such that it communicates with the space, each tube being connected at the other end thereof to an external cooling unit, whereby discharge of heat from the heat sink means is carried out in accordance with circulation of water in the space.

10. The skin cooling device according to claim 6, wherein the heat sink means comprises:
    a confined space provided at the heat emitting portion of the thermoelectric element;
    an air inlet formed at the case to communicate with the space; and
    a tube connected at one end thereof to the case to communicate with the space, the tube being connected to an external exhaust unit at the other end thereof, whereby discharge of heat from the heat sink means is carried out in accordance with exhaustion of air from the space.

11. A skin cooling device comprising:
    a case having a size allowing a user to grasp the case by hand;
    at least one thermoelectric element installed in the case, the thermoelectric element having a heat emitting portion and a heat absorbing portion;
    heat sink means provided at the heat emitting portion of the thermoelectric element;
    cold heat transfer means provided at the heat absorbing portion of the thermoelectric element, and adapted to locally transfer cold heat from the thermoelectric element to the skin, the cold heat transfer means having a tip fitting hole formed at a portion of the case contacting the bottom of the heat absorbing portion of the thermoelectric element; and a skin contact tip separably fitted in the tip fitting hole at one end thereof, the skin contact tip having a fitting portion and a skin contact portion provided with a groove; and
    a lower case detachably coupled to the case to cover the heat absorbing portion of the thermoelectric element, the lower case carrying the cold heat transfer means therein, whereby the skin cooling device can have a common upper construction while being capable of using various types of cold heat transfer means by replacing the lower case with another one carrying another type of cold heat transfer means, wherein the heat absorbing portion of the thermoelectric element is exposed from the case in a downward direction.

12. A skin cooling device comprising:
    a case having a size allowing a user to grasp the case by hand;

at least one thermoelectric element installed in the case, the thermoelectric element having a heat emitting portion and a heat absorbing portion;

heat sink means provided at the heat emitting portion of the thermoelectric element; and cold heat transfer means provided at the heat absorbing portion of the thermoelectric element, and adapted to locally transfer cold heat from the thermoelectric element to the skin, the cold heat transfer means having a tip fitting hole formed at a portion of the case contacting the bottom of the heat absorbing portion of the thermoelectric element; and a skin contact tip separably fitted in the tip fitting hole at one end thereof, the skin contact tip having a fitting portion and a skin contact portion provided with a groove, wherein the cold heat transfer means is provided with a clip for holding a sterilized cotton or gauze at the cold heat transfer means.

* * * * *